(12) United States Patent
Helmlinger

(10) Patent No.: US 9,072,846 B2
(45) Date of Patent: Jul. 7, 2015

(54) MEDIUM DISPENSER

(75) Inventor: Michael Helmlinger, Radolfzell-Boehringen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 42 days.

(21) Appl. No.: 14/006,120

(22) PCT Filed: Apr. 5, 2012

(86) PCT No.: PCT/EP2012/056351
§ 371 (c)(1),
(2), (4) Date: Sep. 19, 2013

(87) PCT Pub. No.: WO2012/136805
PCT Pub. Date: Oct. 11, 2012

(65) Prior Publication Data
US 2014/0008384 A1 Jan. 9, 2014

(30) Foreign Application Priority Data

Apr. 7, 2011 (DE) .......................... 10 2011 007 008

(51) Int. Cl.
*A61M 15/00* (2006.01)
(52) U.S. Cl.
CPC .............. *A61M 15/00* (2013.01); *A61M 15/009* (2013.01); *A61M 2205/825* (2013.01); *A61M 2205/8256* (2013.01); *A61M 15/001* (2014.02); *A61M 15/008* (2014.02); *A61M 2205/332* (2013.01); *A61M 15/005* (2014.02)
(58) Field of Classification Search
USPC ............ 222/23, 39, 113; 128/200.14, 200.23, 128/204.23, 205.23
See application file for complete search history.

(56) References Cited

U.S. PATENT DOCUMENTS

| 2,777,607 | A | * | 1/1957 | Bellandi .......................... 222/39 |
| 5,363,842 | A | | 11/1994 | Mishelevich et al. |
| 5,482,030 | A | * | 1/1996 | Klein ........................ 128/200.23 |
| 5,676,129 | A | * | 10/1997 | Rocci et al. .............. 128/200.23 |
| 5,692,492 | A | | 12/1997 | Bruna et al. |

(Continued)

FOREIGN PATENT DOCUMENTS

| CN | 101405045 A | 4/2009 |
| EP | 0 617 628 A1 | 10/1994 |

(Continued)

OTHER PUBLICATIONS

Form PCT/ISA/210 International Search Report mailed Nov. 26, 2012 (10 pages).

(Continued)

*Primary Examiner* — Donnell Long
(74) *Attorney, Agent, or Firm* — Flynn, Thiel, Boutell & Tanis, P.C.

(57) ABSTRACT

A portable medium dispenser for discharging liquid, pasty or powdery media, having a housing with a discharge opening, a medium reservoir for accommodating the medium before discharge, and an actuating handle, by which a feeding process can be effected during which medium is fed from the medium reservoir to the discharge opening.

The dispenser includes a detecting device for detecting a shaking movement, the detecting device including an optical or acoustic output device and being designed to transfer the output device from a first state into a second state in response to a manual shaking of the dispenser.

9 Claims, 4 Drawing Sheets

(56) References Cited

U.S. PATENT DOCUMENTS

| | | | |
|---|---|---|---|
| 5,957,125 A * | 9/1999 | Sagstetter et al. | 128/200.23 |
| 6,202,642 B1 | 3/2001 | McKinnon et al. | |
| 6,981,499 B2 * | 1/2006 | Anderson et al. | 128/200.23 |
| 2002/0090601 A1 | 7/2002 | Strupat et al. | |
| 2002/0189612 A1 * | 12/2002 | Rand | 128/200.23 |
| 2005/0022806 A1 * | 2/2005 | Beaumont et al. | 128/200.14 |
| 2005/0066961 A1 * | 3/2005 | Rand | 128/200.14 |
| 2005/0076904 A1 * | 4/2005 | Jones et al. | 128/200.23 |
| 2005/0274378 A1 * | 12/2005 | Bonney et al. | 128/200.23 |
| 2007/0135756 A1 | 6/2007 | Kohlbrenner et al. | |
| 2007/0277817 A1 * | 12/2007 | Innocenzi | 128/200.23 |
| 2009/0151721 A1 | 6/2009 | Spaargaren et al. | |

FOREIGN PATENT DOCUMENTS

| | | |
|---|---|---|
| GB | 2469068 A | 10/2010 |
| WO | WO 2008/142015 A2 | 11/2008 |

OTHER PUBLICATIONS

Office Action of German Patent Office issued in German Application No. 10 2011 007 008.7 dated Jan. 4, 2012 (5 pages).

Chinese Office Action dated Dec. 4, 2014 and Chinese Search Report dated Nov. 25, 2014 of the Chinese Patent Office issued in Application No. 201280017294.8 with English translation of the Search Report (17 pages).

* cited by examiner

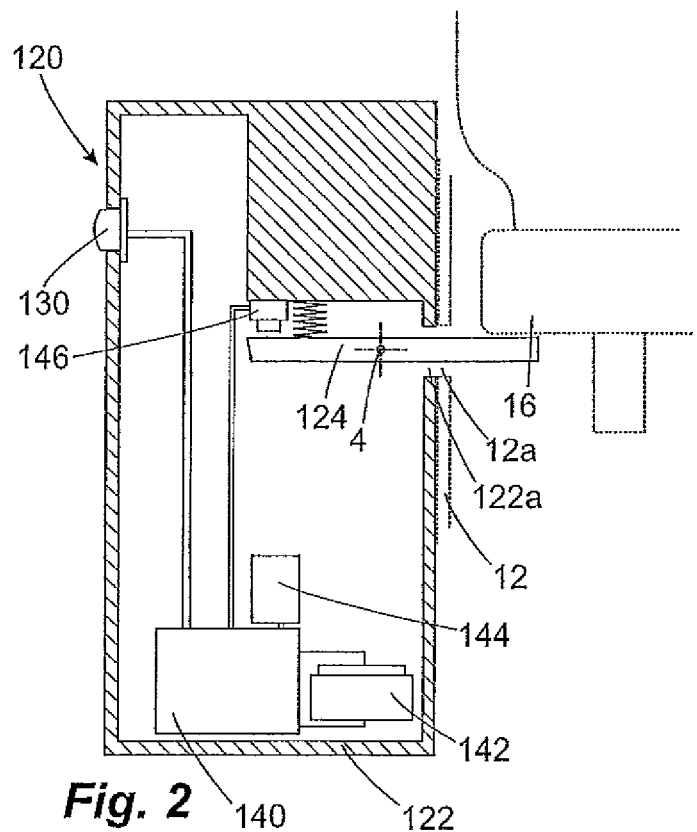
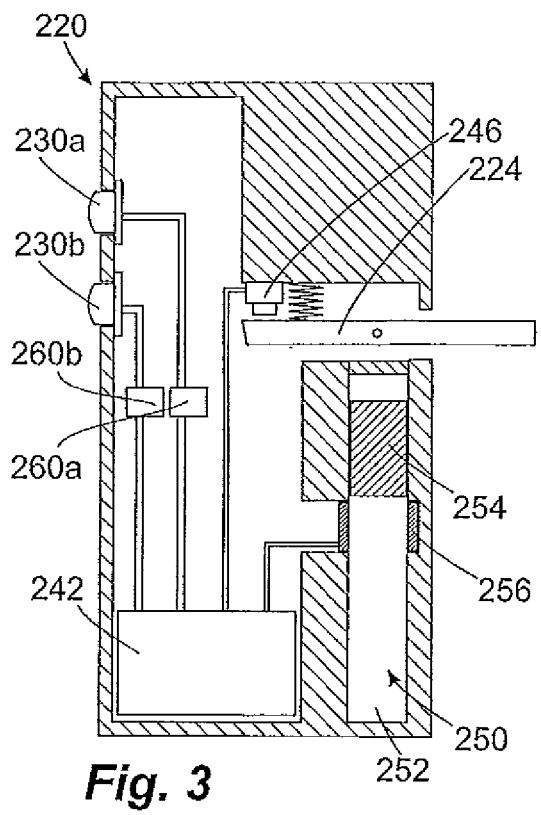
Fig. 2
Fig. 3

MEDIUM DISPENSER

FIELD OF APPLICATION AND PRIOR ART

The invention relates to a portable medium dispenser for discharging liquid, pasty or powdery media, comprising a housing having a discharge opening, comprising a medium reservoir for accommodating the medium before discharge, and comprising an actuating handle, by means of which a feeding process can be effected, during which medium is fed from the medium reservoir to the discharge opening.

Generic medium dispensers are known in general from the prior art. They are used for example for the handling of paints or cosmetic liquids. In particular, the present invention relates to generic dispensers which are intended for the discharge of pharmaceutical media. The medium held available in a generic dispenser can be discharged by means of the actuating handle, wherein the conveying process necessary for this can be supplied by the energy of the actuation or can also be effected by an electrical energy or a propellant, which is likewise held available.

A large number of media to be discharged consist of a plurality of components, which are intended to be discharged in mixed form. Such media can be present, for example, in the form of suspensions or emulsions. They may also be present in the form of homogeneous mixtures however. With all these media which consist of a plurality of components, there is the problem that they may separate over a relatively long period of time in the medium store, such that, when the medium is discharged, the desired mixing ratio is not achieved.

In the case of dispensers that are provided for the discharge of such media, it is usual for these dispensers to be supplied together with handling instructions indicating that the medium dispenser is to be shaken before discharge. However, tests carried out in the field of dispensers containing pharmaceutical media have shown that this instruction is not taken sufficiently seriously by a considerable proportion of users, such that the media are discharged without prior shaking of the medium dispenser or after insufficient shaking of the dispenser.

OBJECT AND SOLUTION

The object of the invention is therefore to provide a medium dispenser of the generic type, which increases the likelihood that the user discharges the medium in the desired mixing ratio of the components of the medium.

This is achieved in accordance with the invention in that the medium dispenser comprises a detecting device for detecting a shaking movement, said detecting device comprising a haptic, optical or acoustic output device and being designed in such a way that it transfers the output device from a first state into a second state in response to manual shaking of the dispenser.

A medium dispenser according to the invention informs the user as to whether the dispenser has been shaken to a sufficient extent. This can be achieved optically, for example via an LED activated or deactivated in response to the shaking process, or also acoustically, for example via an acoustic signal transmitter. It has been found that dispensers which provide information concerning the executed shaking process are not normally used in an unshaken or insufficiently shaken state. Whereas the information in the handling instructions for dispensers, which is often rather vague and generally concerns the number of shaking processes or the shaking period, cannot clearly indicate to the user the extent to which the dispenser actually has to be shaken due to its vagueness, a signal that is clearly identifiable for the user and that indicates the state of readiness leads to sufficient shaking and therefore to discharge of the medium as intended.

The detecting device of a dispenser according to the invention is designed in such a way that it responds in the desired manner to a shaking process. Here, a large number of variants are conceivable.

A particularly simple design is formed in such a way that the detecting device has an indicator space which is completely isolated with respect to the surrounding environment and has an at least partly transparent wall, wherein this forms an optical output device and is at least partly visible for a user, wherein an indicator medium is arranged within the indicator space and changes its appearance as a result of the shaking process.

With such an embodiment, an indicator space that is completely isolated from the medium reservoir is thus provided and contains an indicator medium not intended for discharge. This indicator medium changes its appearance as a result of shaking. The user can see through the transparent wall into the indicator space and can therefore identify the state of the indicator medium. Here, the indicator medium is designed in such a way that it reassumes its original appearance once the shaking process is terminated, wherein it preferably returns slowly and over a period of preferably a few minutes to its original appearance as a result of the type of indicator medium.

In accordance with a particularly advantageous embodiment, so that the indicator medium changes its appearance as a result of shaking, the indicator medium is an emulsion or suspension, that is to say a medium consisting of a carrier liquid and a second liquid or particulate matter. Similarly to the manner known from souvenir snow globes, in which snowfall can be caused by shaking, particulate matter or bubbles of the second liquid can thus be swirled up by shaking the dispenser, such that it changes the look of the indicator medium, at least in the region visible for the user. For example, a colorless carrier liquid could thus be provided, in which colored particulate matter is contained. In the rest state of the dispenser, this particulate matter settles on the base of the indicator space, said base preferably not being visible for the user. By shaking the dispenser, it is swirled up however, such that it enters the visible region. Besides the viewing window, through which the user can see into the indicator space, a comparison colored area may additionally be provided. As soon as the dispenser has been shaken to the sufficient extent, the indicator medium visible through the viewing window has the color of the comparison colored area.

With this embodiment with indicator medium, the appearance of the liquid in the liquid reservoir is the indicator for sufficient mixing in the medium store of the medium dispenser. An adaptation to different media usable in the medium reservoir can be achieved by adapting the viscosity or density of the liquids in the liquid reservoir or by adapting the density or the quantity of the particulate matter. The sedimentation rate of the particulate matter can thus be influenced and in turn influences the period of time over which, after a shaking process, the particulate matter is visible for the user through the viewing window.

In accordance with another variant of a medium dispenser according to the invention, the output device is formed as an optical output device and comprises a display element movable mechanically with respect to the housing, wherein the position of the display element can be changed by shaking the detecting device and is externally visible for a user.

With such a dispenser, a portion that can be displaced with respect to the housing is provided in the form of the display element, the position of which is visible for the user. This visibility can be assisted in particular in that an area highlighted in color is provided on the display element and is or isn't externally visible depending on the position of the display element. Two such colored areas are preferably provided, wherein a first, preferably red, colored area symbolizes an insufficiently shaken state, and a second, preferably green, colored area symbolizes a sufficiently shaken state. In the unshaken state, only the first colored area is visible or predominantly visible, whereas, in the sufficiently shaken state, only the second colored area is visible or predominantly visible.

The position of the display element can be changed by shaking. In this case, a displacement of the display element that is produced when the dispenser is shaken due to the inertia of the display element can be used in particular.

The display element is preferably movable between a first position, which symbolizes a first shaken state, and a second position, which symbolizes a second shaken state. Here, the display element can be displaced only in the direction of the second position by shaking. With such an embodiment, the display element can therefore be displaced between a first position symbolizing the unshaken or insufficiently shaken state and a second position symbolizing the sufficiently shaken state, wherein, as a result of the shaking of the medium dispenser, merely a displacement in the direction of the second position is implemented. This unidirectional movement of the display element caused by the shaking process can be achieved in particular by detent elements or a detent ladder, which can ensure the unidirectionality in particular by means of a sawtooth-like design. In order to displace the display element into the second position, it must be moved in steps over a plurality of shaking periods in the direction of the second position, wherein a displacement back in the direction of the first position does not initially occur or cannot be caused by shaking alone.

In order to ensure however that the display element is not paused for a relatively long period of time in the second position and therefore, once a specific period of time has elapsed, incorrectly displays a readiness for discharge, reset means are preferably provided which cause the display element to be transferred back into the first position from a position deviating from the first position as soon as a holding period has elapsed. Such a holding period may preferably be a period of a few seconds, for example between 10 seconds and 240 seconds. If, after shaking the dispenser, the dispenser therefore stands still without execution of a discharge process, the display element reverts back to its first position once this holding period has elapsed. Embodiments in which a return movement merely from the second position into the first position once the holding period has elapsed and also in which any position of the display element deviating from the first position leads to the aforementioned reset once a holding period has elapsed are conceivable.

A constructional possibility of implementing this feature lies in providing the detent ladder, which ensures the unidirectionality, with one or more slightly inclined detent teeth, along which an engagement portion engaged with the detent ladder slides over the holding period so as to completely lose the contact with the respective inclined detent tooth once the holding period has elapsed.

Furthermore, an effective coupling between the actuating handle and the display element may also be provided, as a result of which the display element is displaced back into the first position when the actuating handle is actuated. Once a discharge process has been carried out, a state of the display element is thus automatically produced again and symbolizes the need for shaking.

Besides the aforementioned purely mechanical solutions, electrically assisted solutions of a medium dispenser according to the invention are also conceivable.

The detecting device of the medium dispenser with such solutions therefore preferably has an output device, which is formed as an electrically activatable output device. In the case of an acoustic output device, this may therefore contain a loudspeaker. In the case of an optical output device, one or more LEDs is/are preferably provided, which indicate the current state of the dispenser. A haptic output device could be provided for example in the form of a vibrator, which is designed in such a way as is known by mobile telephones.

In the case of the use of LEDs or another optical output device, it is particularly advantageous if the output device is designed to indicate at least three states differentiable for the user. This may be achieved for example via an LED which, besides the switched-off state, can also output light in two different colors. An embodiment with two LEDs is also able to indicate the desired three differentiable states. The possibility of indicating three differentiable states via the output device makes it possible, besides a rest state, to also make a further state visible for the user, in which the onset of the shaking process has been registered, however the shaking process performed is not yet sufficient. In the embodiment with one LED, this could, for example, assume a first color with the onset of the shaking process and could assume a second color after sufficient shaking.

To supply current to the electrical output device, the medium dispenser can be equipped with an energy store, such as a battery or an accumulator, which is preferably already sufficiently charged in the supplied state in order to provide sufficient energy over the period of use of the dispenser. A disadvantage here however is that, with generic dispensers, the period of time between production and supply to the user and/or the period of time within which the dispenser is used by the user may be many months, such that an accumulator loaded once or a battery loaded once may be unloaded before the medium reservoir of the medium has been completely emptied.

In accordance with an advantageous embodiment of the medium dispenser, the detecting device comprises an energy store for storing electrical energy and an energy convertor, which, by shaking, converts introduced mechanical energy into electrical energy, wherein the electrical energy thus produced is stored in the energy store. With such an embodiment, the energy introduced into the system by the shaking process is therefore itself used to load an energy store. The energy store may be the accumulator already mentioned. Energy stores that allow merely a short-term storage of energy, such as a capacitor, may also be used however. The energy convertor can be formed differently. For example, the embodiment known from "shake-type torch lights", in which a magnet is displaced relative to a coil such that a voltage is induced in the coil, is thus conceivable. The movement of the magnet or of the coil can be linear or rotary here, for example. A generation of electrical energy based on piezo technology is also conceivable, for example by means of a piezoelectric bending transducer.

The conversion of the energy introduced mechanically into the system into electrical energy enables a particularly simple embodiment of a medium dispenser according to the invention. With this embodiment, the output device is connected to the mentioned energy store via a circuit which causes a separation of the energy store from the output device as long as the energy stored in the energy store does not exceed a specific measure. Only when a limit value, which for example may be a voltage limit value or an energy limit value, has been exceeded is current supplied to the output device. With such an embodiment, in which the limit value switch forms a comparator so to speak, it is therefore possible to dispense completely with a microprocessor where necessary, since merely the energy introduced into the energy store by the shaking in conjunction with the limit value switch makes it possible for the user to identify whether he has already shaken the dispenser to a sufficient extent.

Due to the use of two limit value switches which have different limit values and influence the output device differently, the above-mentioned embodiment can also be achieved, in which, with the onset of the shaking process, a first LED is lit, and, after a sufficiently long shaking process, a second LED is lit, wherein this second LED signals the readiness for discharge.

It is particularly advantageous if, in this embodiment, the actuating handle is effectively coupled to the energy store in such a way that this is unloaded as soon as the actuating handle is actuated. The actuating handle can therefore short circuit a capacitor used as an energy store, for example indirectly or directly. After the discharge process, the energy store is therefore empty again, such that a new shaking process is required in order to again activate the readiness LED.

Besides such a comparatively simple embodiment, an embodiment of a medium dispenser according to the invention in which the detecting device comprises a microprocessor, which is connected to the output device for control thereof is also possible. Such a microprocessor can be supplied with electrical energy by an energy store, which is already loaded in the supplied state. However, it may also be supplied with electrical energy by an energy store that is loaded as a result of the shaking process of the dispenser.

The microprocessor, similarly to the above-mentioned limit value switch, can, with the presence of an energy store loaded by shaking, make the loading level of said energy store a criterion for the activation of the output device. Due to the use of a microprocessor, an embodiment is also conceivable however in which an acceleration sensor delivering even an insignificant energy amount is used, of which the sensor data is evaluated by the microprocessor in order to detect whether the dispenser has been shaken to a sufficient extent. In this instance, in the simplest case, the period of time within which the dispenser has been shaken could be evaluated. The number of shaking periods could also be evaluated. It is most advantageous however if the introduced energy is detected by means of the acceleration sensor and is added cumulatively until a desired limit value has been reached.

Even with such an embodiment with a microprocessor, effective coupling with the actuating handle may be provided, as a result of which, after an actuation process or a defined number of actuation processes, the microprocessor is reset, such that it initially starts again from the unshaken state of the dispenser for a renewed discharge process.

The detecting device can be integrated directly into the housing of the medium dispenser, which preferably also contains the medium reservoir. Here, an electronics system provided in the dispenser where necessary can also take on the described functions. In the case of dispensers that electronically enable a prevention of a discharge process, for example in order to prevent overdosing, this prevention may also be provided as long as the dispenser has not yet been shaken to a sufficient extent. This lends itself in particular in the case of dispensers in which the feeding process is supplied electrically, and for example in dispensers in which the medium is atomized by means of a vibration device and in doing so is discharged. In these cases, the supply of the feeding device or of the vibration device with electrical energy can be made dependent on whether the dispenser has been shaken beforehand to a sufficient extent.

It is particularly advantageous if the detecting device is formed as a separate module, in particular as a separate module with a module housing separate from a main housing of the medium dispenser. The separate embodiment of the detecting device as a module makes it possible to use this in unchanged or largely unchanged form in various dispensers. This modular embodiment is to be understood to mean that all components necessary for the functioning of the detecting device, that is to say in particular the output device and any mechanism that causes a change of state of the output device upon shaking, are comprised in one structural unit that can be handled as a whole. If this comprises a separate module housing, attachment to the outer face of a dispenser is also possible.

The identical detecting device or at least detecting devices that are merely modified slightly can thus be used on different dispensers. It is also possible for the user to use a detecting device successively with a number of medium dispensers.

The coupling device, by means of which the separate module can be connected to the main housing, can be designed differently depending on who is supposed to carry out the change. In the case of a detecting device that is provided for a number of dispenser types, but is not to be exchangeable by the end user, the coupling device can be arranged so as to be inaccessible from outside. In the case of intended exchange by the user, the coupling device is preferably accessible for the user and easy to handle.

BRIEF DESCRIPTION OF THE DRAWINGS

Further advantages and aspects of the invention will emerge from the following description of preferred exemplary embodiments of the invention, which are explained on the basis of the figures, in which:

FIG. 2 shows a first embodiment of the detecting device of the medium dispenser of FIG. 1.

DETAILED DESCRIPTION OF THE EXEMPLARY EMBODIMENTS

Figure 1:
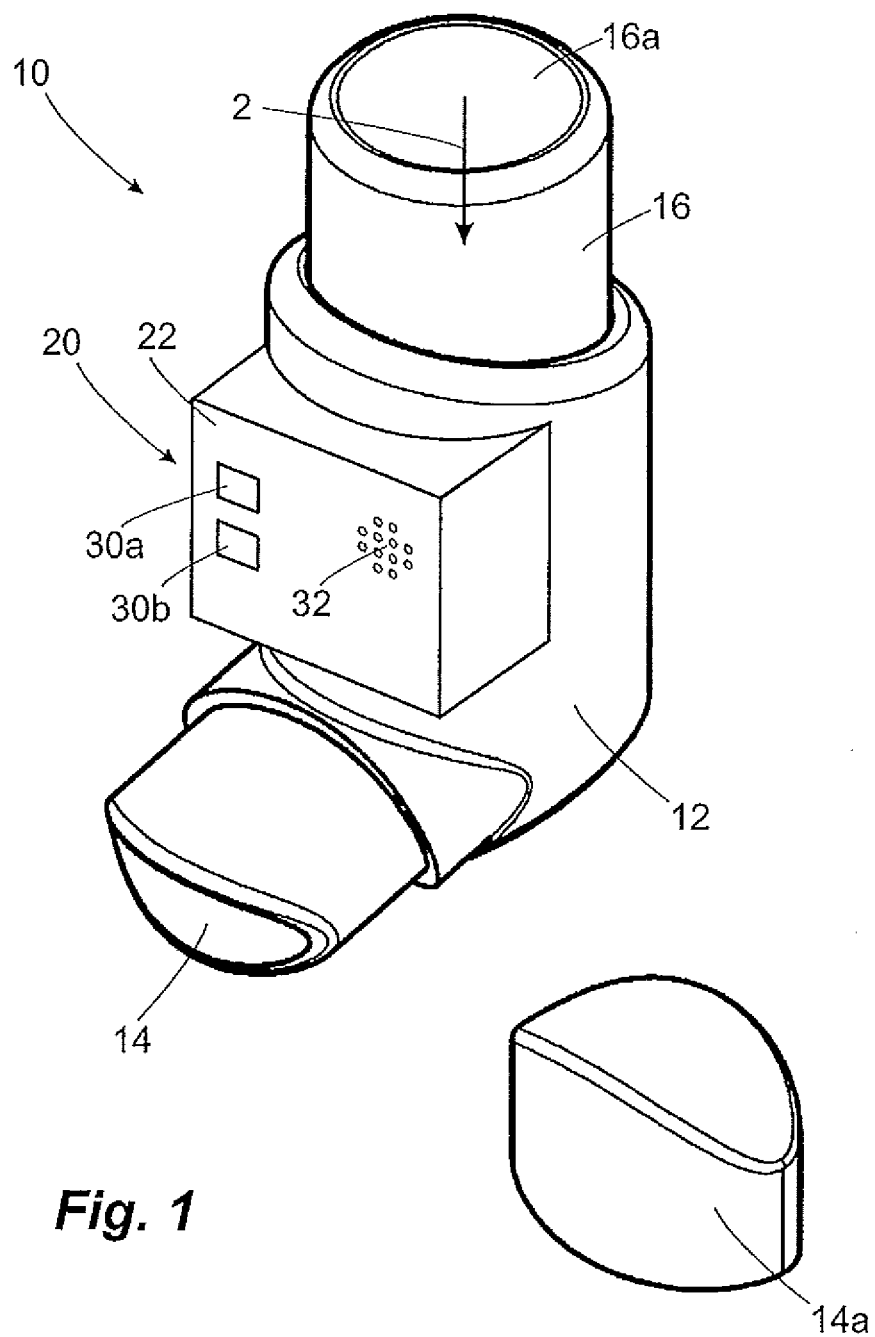
FIG. 1 shows a medium dispenser according to the invention with a detecting device according to the invention.

FIG. 1 shows a medium dispenser 10 according to the invention. This is formed in the present case as a metered dose inhaler (MDI), wherein this embodiment is to be understood in the present case as merely representative for a large number of possible designs of a medium dispenser according to the invention.

The medium dispenser 10 has a housing 12 with a discharge opening 14, which can be covered by a cap 14a, for oral administration of a drug. A medium reservoir 16 is provided for this drug and is inserted into the housing 12 and can be pressed down as a whole in an actuation direction 2 in order to effect a discharge process. The upper terminating face 16a of the medium reservoir 16 thus forms the actuating handle 16a for triggering a discharge process. In the case of the illustrated dispenser 10, this discharge process is caused after opening an outlet valve as a result of the actuating movement by a propellant. The specific feature according to the invention that will be explained hereinafter can also be used however in dispensers in which the energy necessary for discharge is introduced for example directly via the mechanical actuation or originates from an electrical energy store.

A drug, in the form of a suspension, to be discharged is contained within the medium reservoir 16. It is desirable for this suspension to be mixed before a discharge process by shaking the dispenser 10.

A detecting device 20 is provided on the front face of the medium dispenser 10 and is used for detection of a shaking movement. This detecting device 20 in the exemplary embodiment shown in FIG. 1 has its own module housing 22 and two LEDs 30a, 30b and also a loudspeaker 32.

As soon as the dispenser 10 is shaken by a user, the LED 30a is supplied with current, such that it lights up and indicates to the user that the shaking process has been registered. As soon as the dispenser 10 has been shaken to a sufficient extent in order to cause a desired mixing of the pharmaceutical medium in the medium reservoir 16, for example for a period of approximately 20 seconds at a frequency of approximately 2 Hz, the second LED 30b is also supplied with current and an acoustic signal is output via the loudspeaker 32, such that the user knows that the performed shaking is sufficient. The user can then place the discharge opening 14 against his mouth in the intended manner and can implement a discharge of the medium from the liquid reservoir 16 by means of the actuating handle 16a.

The detecting device 20 can be formed as a separate module, which can be coupled to the dispenser housing 12 in the fully assembled state. To this end, mechanical coupling interfaces (not illustrated in greater detail) can be provided on the main housing 12 and the module housing 22. Furthermore, for registration of a discharge process, through-holes can be provided in the module housing 22 and the main housing 12, through which the detecting device detects the movement of the actuating handle 16a mechanically or electrically.

FIG. 2 shows a first variant 120 of a detecting device 20. This detecting device 120 has a housing 122, which is largely closed and allows external attachment to a largely unchanged conventional dispenser. Within the housing 122, a microprocessor 140 is provided, which is supplied with electrical energy by a battery 142. This microprocessor 140 is additionally connected to an acceleration sensor 144 and also a display LED 130.

When the dispenser 10 is shaken by the user, this is thus detected by the sensor 144, and corresponding sensor output data is relayed to the microprocessor 140. The microprocessor evaluates the captured data, for example in terms of the number of shaking periods and/or in terms of the intensity of the shaking. As soon as the shaking process has reached a measure that ensures sufficient mixing of the liquid in the medium reservoir 16, the LED 130 is supplied with current, such that the user thus learns that the dispenser 10 is now fully prepared for a discharge process.

A button 146 is furthermore also connected to the microprocessor 140 and can be pressed down by a pivot lever 124. The pivot lever is pivotable about a pivot axis 4 fixed on the housing. The end of the pivot lever pointing away from the button 146 protrudes through a recess 122a in the housing 122 and also through a recess 12a in the housing 12, such that it is pivoted in a clockwise direction when the medium reservoir 16 is pressed down. The button 146 makes it possible to use the discharge process performed to reset the microprocessor 140. For a subsequent, next discharge process, the dispenser 10 therefore has to be shaken again until the readiness for discharge is displayed by the LED 130.

FIG. 3 shows a further variant 220 of a detecting device 20 according to the invention. This detecting device 220 again comprises two LEDs 230a, 230b, which are used in the manner explained in FIG. 1 to provide information to the user. Furthermore, the detecting device 220 comprises an energy store 242, which, by contrast with the battery 142 of the embodiment of FIG. 2, is not loaded however in the supplied state of the dispenser. It is instead connected to an energy convertor 250. The convertor 250 has a vertically extended shaft 252 in which a magnet 254 is movably mounted. This shaft 252 is surrounded by a coil 256, in which current is induced when the magnet 254 moves in the shaft 252. The movement of the magnet 254 is caused by shaking the dispenser 10, such that this shaking loads the energy store 242 formed, for example, by capacitor plates.

As soon as the energy provided in the energy store 242 exceeds a predefined limit value, this leads to a closure of a limit value switch 260a, such that, from this moment, the LED 30a is supplied with current. The corresponding limit value is set very low, such that, in the ideal case, the LED 30a lights up after just one to two shaking movements. The user is thus advised that the onset of the shaking process has been registered. The second limit value switch 260b, which connects the energy store 242 to the LED 30b, closes at a much higher limit value. Only when the energy in the energy store 242 has reached a level that is reached for example by moderate to severe shaking of the dispenser for 20 seconds does the switch 260b close, such that the LED 230b is then activated. This signals to the user that he can now begin with the discharge process by pressing the actuating handle 16a downward.

Similarly to the detecting device of FIG. 2, the detecting device of FIG. 3 also comprises an additional button 246, which, via a lever 224, forms an effective coupling to the medium reservoir 16. As soon as the medium reservoir 16 is pressed, the button 246 short circuits the energy store 242 briefly, for example by connecting two capacitor plates of the energy store 242. By actuating the dispenser 10, a starting state is thus achieved again, in which the energy store 242 is unloaded and, starting from which, renewed shaking is initially required in order to shift the dispenser 10 into a state ready for discharge.

Figure 3A:
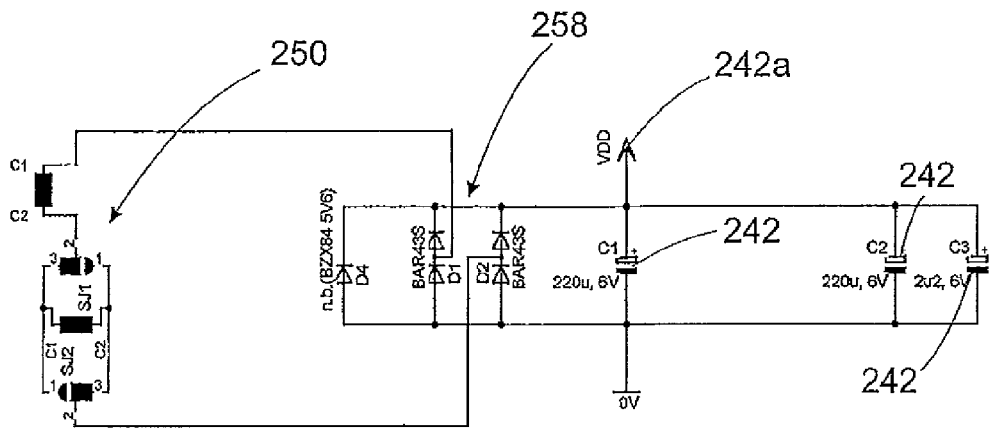
FIG. 3 shows a second embodiment of the detecting device of the medium dispenser of FIG. 1, FIGS. 3a, 3b show an alternative circuit for use in the detecting device in the exemplary embodiment of FIG. 3.
Figure 3B:
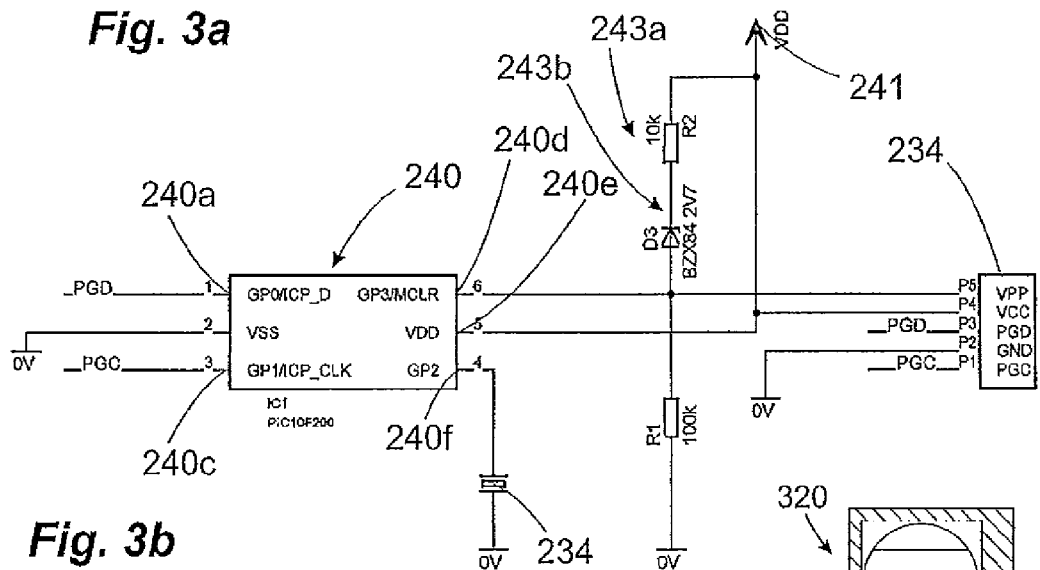

FIGS. 3a and 3b show an electronic circuit, by means of which the functionality described on the basis of FIG. 3 can be provided.

As is illustrated in FIG. 3a, the circuit has a mechanoelectrical energy convertor 250, which, upon shaking of the dispenser, generates an a.c. voltage. A bridge rectifier 258, which converts the a.c. voltage into a d.c. voltage which is used to load the capacitors 242 acting as energy stores, is connected to the energy convertor 250. The capacitors 242 act as energy integrators. Due to continued shaking movement, the electrical energy stored in the capacitors can be increased. With the stored energy, the output voltage of the capacitors 242 at the output connection 242a also increases.

The output connection 242a of the capacitors 242 is connected to an input connection 241 of an evaluation and display circuit, which is illustrated in FIG. 3b. The input connection 241 is connected for the purpose of current supply to a display, which is designed to present the words "Shake" and "Ready". Equally, LEDs could also be used here. The input connection 241 is also connected for the purpose of current supply directly to a supply connection 240e of a microprocessor 240. The input connection 241 is additionally also connected indirectly to a digital connection 240d of the microprocessor via a voltage divider 243a and a zener diode 243b.

The microprocessor 240 has three outputs 240a, 240c, 240f. A buzzer 234 is connected to the output 240f. The outputs 240a, 240c are connected to the display and make it possible for the word "Shake" to appear thereon by means of the connection 240a and for the word "Ready" to appear thereon by means of the connection 240c.

The circuit of FIGS. 3a and 3b functions as follows: by shaking the dispenser, the energy convertor 250 generates an electric alternating current, which is rectified by the bridge rectifier 258 and is then supplied to the capacitors 242. With a rise of the electrical energy stored in the capacitors, the voltage at the output connection 242a and at the input connection 241 also rises. As soon as this voltage has reached a level sufficient for operation of the microprocessor 240, said microprocessor is started and from this moment monitors the digital input 240d. At the same time, the word "Shake" is displayed on the display via the output 240a. If, by continued shaking, the energy level in the capacitors 242 and with it the voltage level at the input connection 241 is increased further, the voltage on the other side of the voltage divider 243a and of the zener diode 243b also reaches a level that leads to detection of the voltage at the digital input 240d of the processor 240.

This is understood by the processor to mean that the dispenser has been shaken sufficiently intensely. This state can be indicated to the user via the outputs 240c and 240f by optical display of the word "Ready" on the display by buzzing the buzzer 234. The user can now use the dispenser as intended.

Figure 4:
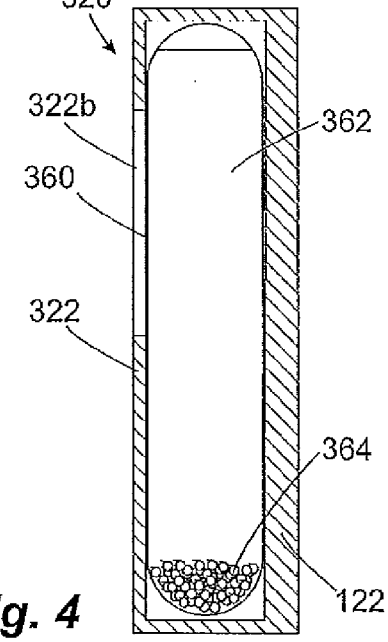
FIG. 4 shows a third embodiment of the detecting device of the medium store of FIG. 1, and FIGS. 5a-5c and FIG. 6 show a fourth embodiment of the detecting device of the medium dispenser of FIG. 1.

FIG. 4 shows a further embodiment of a detecting device 320 provided in accordance with the invention on a dispenser 10. This detecting device is embodied in a particularly simple manner. It has a transparent reservoir 360 for an indicator medium, said reservoir being completely isolated with respect to a surrounding environment. The indicator medium, which, besides a liquid 362, also contains a large number of solid particles 364, is located in this reservoir 360. The housing 322 is provided in an upper region with a window 322b, through which an upper region of the reservoir 360 can be seen.

If the dispenser 10 is now shaken together with the detecting device 320, the suspended particles 364, of which the density is slightly greater than that of the liquid 362, are swirled up, such that they are distributed largely homogeneously in the liquid 362. The swirled-up suspended particles 364 are visible for the user through the window opening 322b, wherein they are provided for this purpose in particular with a characteristic coloring, for example a green coloring. If the content of the reservoir 360 is perceived by the user through the opening 322b as being colored accordingly, he knows that the dispenser has been shaken to a sufficient extent. He can then use the dispenser 10 as intended.

The embodiment in FIGS. 5a to 5c and 6 again illustrates a mechanical solution of the detecting device in a highly schematic form. This detecting device 420 will be explained hereinafter firstly with reference to FIG. 5a. The changes to the detecting device 420, which are caused by shaking the dispenser 10, will then be explained on the basis of the transition from the state in FIG. 5a via the state in FIG. 5b to the state in FIG. 5c.

A display pin 470 with an approximately circular cross section is positioned within the housing 422 of the detecting device 420. The side of the display pin pointing towards the front face and a window 422c arranged there has a green colored area 472a and a red colored area 472b. As can be seen with reference to FIG. 5a, the red colored area 472b is arranged behind the window 422c in the starting state, such that the user knows that the detecting device 420 is in the unshaken starting state. The display element 470 is movable in two ways with respect to the housing 422. On the one hand, it can be displaced in a longitudinal direction 6 against the force of a spring 480. On the other hand, it can be rotated about an axis of rotation 8, wherein the spring 480 is twisted in this case. On its rear face, the display element 470 illustrated again in FIG. 6 is provided with a sawtooth-like detent ladder 474. In the manner visible from FIG. 5a, an end 424a of a pivot lever 424 provided with a cant engages in this detent ladder 474. The pivot lever 424 is delimited here in terms of its pivotability by a stop 426. A pivoted shift of the lever 424 in an anti-clockwise direction counteracts a second spring 482.

Figure 5A:
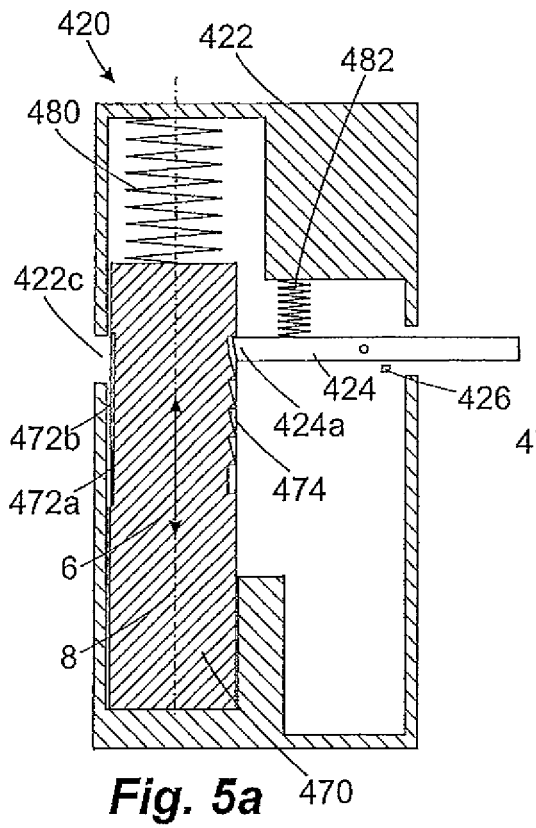
Figure 5B:
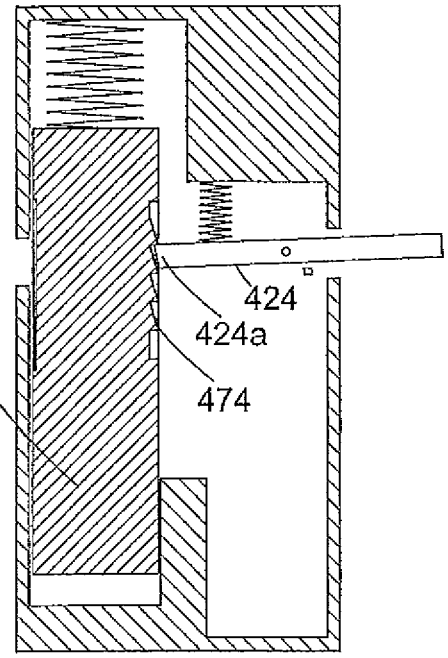
Figure 5C:
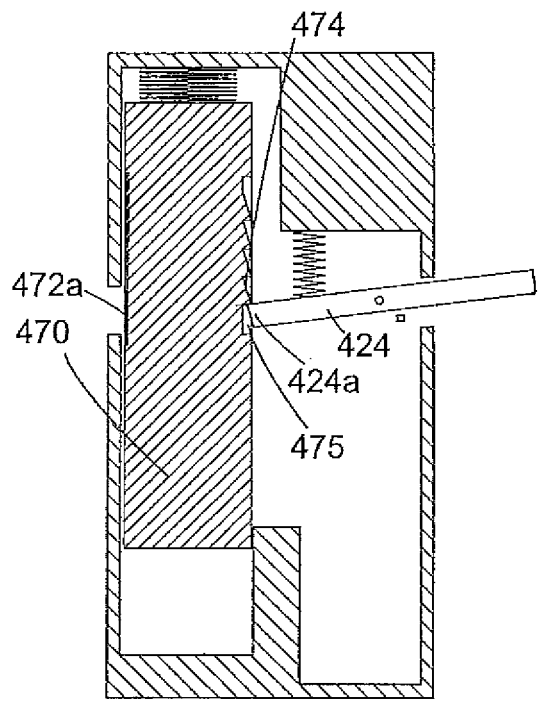
Figure 6:
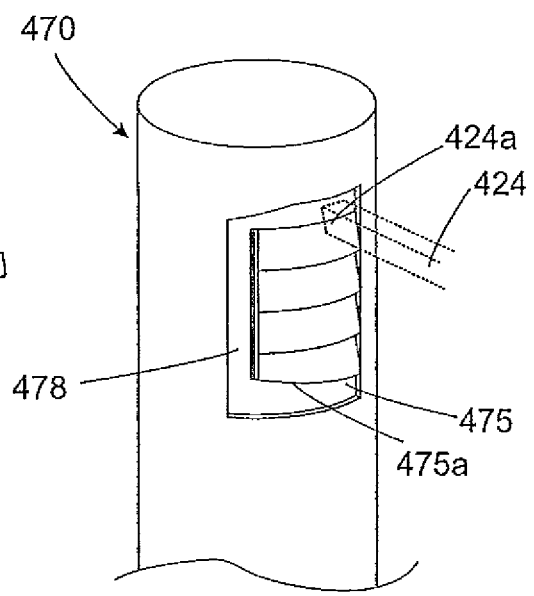

If, starting from the state in FIG. 5a, the dispenser 10 is shaken, a movement of the display element 470 upward is thus caused in conjunction with the inertia of the display element 470, wherein this movement occurs against the compression of the spring 480. If the display element is moved sufficiently far during this process, the end 424a of the pivot lever jumps to a further detent stage of the detent ladder 474. Due to the sawtooth-like configuration of the detent ladder 474, a return of the display element 470 into its starting position in FIG. 5a is then not possible initially. The state in FIG. 5b shows this. If the dispenser 10 with the detecting device 420 has been shaken for a sufficient period of time, the state in FIG. 5c is reached. In this state, the end 424a of the pivot lever 424 has overcome the last detent stage. The green colored area 472a is therefore now positioned behind the window 422c, such that it is signaled to the user that he has shaken the dispenser to a sufficient degree.

If the user now actuates the dispenser, the lever 424 is thus pivoted in a clockwise direction, wherein it is lifted out from the detent ladder 474, such that the display element 470 can spring back into the starting position of FIG. 5a.

In order to ensure that the state illustrated in FIG. 5c, in which the readiness for discharge is signaled to the user, is not maintained for an unlimited period of time, the last rung 475 of the detent ladder 474 is provided with a canted area 475a. Once the state in FIG. 5c has been reached, and should no discharge process be effected, the end 424a of the lever 424 therefore slides slowly along the cant 475a under the force of the springs 480, 482, whilst the display element 470 rotates slowly about the axis 8 and in doing so twists the spring 480. After a period of time, which is defined by various parameters such as the angle of the cant, the properties of the springs and friction, which period of time is preferably between 10 seconds and 240 seconds, the end 424a of the lever 424 thus reaches a non-toothed reset groove 47. As soon as this is the case, the display element 470 springs back into its starting position in FIG. 5a, although no discharge process has been performed.

In order to again reach a discharge-ready state starting from the starting position in FIG. 5a, the user must therefore shake the medium dispenser 10 again.

The invention claimed is:
1. A portable medium dispenser for discharging liquid, pasty or powdery media, comprising:
 a housing having a discharge opening;
 a medium reservoir for accommodating the medium before discharge;

an actuating handle, by which actuating handle a feeding process is effected, during which feeding process medium is fed from the medium reservoir to the discharge opening; and a detecting device for detecting a shaking movement, said detecting device comprising a haptic, optical or acoustic output device, the detecting device transferring the output device from a first state into a second state in response to manual shaking of the dispenser, the detecting device comprising an energy store for storing electrical energy and an energy converter, which energy converter, by shaking of the medium dispenser, converts introduced mechanical energy into electrical energy, wherein the electrical energy thus produced loads the energy store, the output device being connected to the energy store via a circuit, which circuit causes a separation of the energy store from the output device as long as the energy stored in the energy store does not exceed a limit value.

2. The medium dispenser as claimed in claim 1, wherein the output device comprises an electrically activatable output device.

3. The medium dispenser as claimed in claim 2, wherein the output device is formed as an optical output device designed to indicate at least three differentiable states.

4. The medium dispenser as claimed in claim 1, wherein the detecting device comprises a microprocessor connected to the output device for control thereof.

5. The medium dispenser as claimed in claim 1, wherein the detecting device is formed as a separate module with a module housing separate from the housing of the dispenser.

6. The medium dispenser as claimed in claim 1, wherein the circuit includes a limit value switch electrically connecting the output device to the energy store, and when the energy stored in the energy store exceeds the limit value, the limit value switch closes and transfers the output device from the first state to the second state.

7. A medium dispenser for discharging liquid, pasty or powdery media, comprising:

a housing having a discharge opening;

a medium reservoir for accommodating the medium before discharge;

an actuating handle, by which actuating handle a feeding process is effected, during which feeding process medium is fed from the medium reservoir to the discharge opening; and a detecting device for detecting a shaking movement, said detecting device comprising an optical output device, the detecting device transferring the output device from a first state into a second state in response to manual shaking of the dispenser, the detecting device having an indicator reservoir completely isolated with respect to the surrounding environment and having a transparent wall, the indicator reservoir forming the optical output device and being at least partly visible to a user, and a liquid containing solid particles is disposed within the indicator reservoir and changes its appearance as a result of shaking of the medium dispenser.

8. A portable medium dispenser for discharging liquid, pasty or powdery media, comprising:

a housing having a discharge opening;

a medium reservoir for accommodating the medium before discharge;

an actuating handle, by which actuating handle a feeding process is effected, during which feeding process medium is fed from the medium reservoir to the discharge opening; and a detecting device for detecting a shaking movement, said detecting device comprising an optical output device, the detecting device transferring the output device from a first state into a second state in response to manual shaking of the dispenser, the output device comprising a display element movable mechanically with respect to the housing, wherein a position of the display element is changeable by shaking the detecting device and is externally visible to a user, the display element being movable between a first position symbolizing a first shaken state and a second position symbolizing a second shaken state, wherein the display element is displaceable in the direction of the second position by shaking, the detecting device further comprising a reset arrangement causing the display element to be moved back into the first position from a position deviating from the first position if a holding period has elapsed.

9. A portable medium dispenser for discharging liquid, pasty or powdery media, comprising:

a housing having a discharge opening;

a medium reservoir for accommodating the medium before discharge;

an actuating handle, by which actuating handle a feeding process is effected, during which feeding process medium is fed from the medium reservoir to the discharge opening;

a detecting device for detecting a shaking movement, said detecting device comprising an optical output device, the detecting device transferring the output device from a first state into a second state in response to manual shaking of the dispenser, the output device comprising a display element movable mechanically with respect to the housing, wherein a position of the display element is changeable by shaking the detecting device and is externally visible to a user, the display element being movable between a first position symbolizing a first shaken state and a second position symbolizing a second shaken state, wherein the display element is displaceable in the direction of the second position by shaking, the detecting device further comprising a coupling between the actuating handle and the display element, the coupling displacing the display element into the first position when the actuating handle is actuated.

* * * * *